United States Patent [19]

Chamberlain et al.

[11] 4,281,008
[45] Jul. 28, 1981

[54] PHARMACEUTICAL HETEROCYCLIC COMPOUNDS AND COMPOSITIONS

[75] Inventors: Terence R. Chamberlain, Kimarnock, Scotland; John R. Bantick, Loughborough, England

[73] Assignee: Fisons Limited, London, England

[21] Appl. No.: 127,832

[22] Filed: Mar. 6, 1980

[30] Foreign Application Priority Data

Mar. 20, 1979 [GB] United Kingdom ............... 09835/79

[51] Int. Cl.³ .................... A61K 31/41; A61K 31/35; C07D 311/22; C07D 257/04
[52] U.S. Cl. ................................. 424/269; 260/345.2; 424/283; 542/441; 548/252; 548/253
[58] Field of Search ............... 260/345.2; 548/252, 548/253, 254; 542/413, 441; 424/283, 269

[56] References Cited

U.S. PATENT DOCUMENTS 3,948,955  4/1976  Lee et al. .................... 260/345.2
4,133,889  1/1979  Augstein et al. ............. 260/345.2

Primary Examiner—Nicky Chan
Attorney, Agent, or Firm—Merriam, Marshall & Bicknell

[57] ABSTRACT

The compounds of the formula:

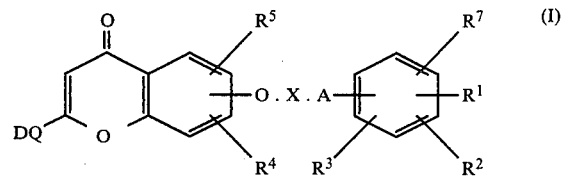

wherein: $R^1$, $R^2$, $R^3$, $R^4$, $R^5$ and $R^7$, which may be the same or different, each represent hydrogen, hydroxy, alkyl or alkoxy of 1 to 6 carbon atoms, amino, acyl or acylamino of 2 to 6 carbon atoms, alkenyl of 2 to 6 carbon atoms, halogen, or alkoxy of 1 to 6 carbon atoms substituted by phenyl, X is a hydrocarbon chain of 1 to 10 carbon atoms optionally substituted by a hydroxy group, A is oxygen or is absent, Q represents a straight or branched alkylene, alkenylene or alkynylene group of 2 to 6 carbon atoms, and D represents carboxy, 5-tetrazolyl or carboxamido-5-tetrazolyl, and pharmaceutically acceptable salts, esters and amides thereof, are pharmaceutically active, being antagonists of the slow reacting substance of anaphylaxis (SRS-A) or its pathological effects.

Pharmaceutical compositions containing the compounds are also described, as well as processes for preparing the compounds.

10 Claims, No Drawings

PHARMACEUTICAL HETEROCYCLIC COMPOUNDS AND COMPOSITIONS

This invention relates to new compounds, methods for their preparation and compositions containing them.

According to our invention we provide compounds of formula I,

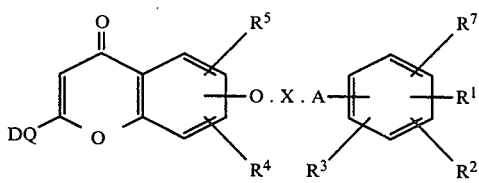

wherein: $R^1$, $R^2$, $R^3$, $R^4$, $R^5$ and $R^7$, which may be the same or different, each represent hydrogen, hydroxy, alkyl or alkoxy of 1 to 6 carbon atoms, amino, acyl or acylamino of 2 to 6 carbon atoms, alkenyl of 2 to 6 carbon atoms, halogen, or alkoxy of 1 to 6 carbon atoms substituted by phenyl, X is a hydrocarbon chain of 1 to 10 carbon atoms optionally substituted by a hydroxy group, A is oxygen or is absent, Q represents a straight or branched alkylene, alkenylene or alkynylene group of 2 to 6 carbon atoms, and D represents carboxy, 5-tetrazolyl or carboxamido-5-tetrazolyl, and pharmaceutically acceptable salts thereof, and esters and amides of those compounds where D represents carboxy.

Where one or more of $R^1$, $R^2$, $R^3$, $R^4$, $R^5$ and $R^7$ represents alkyl or alkoxy, it is preferably of 1 to 4 carbon atoms and is desirably a straight chain alkyl or alkoxy group. Specific preferred alkyl groups are methyl, ethyl, n-propyl, n-butyl, and preferred alkoxy groups are the alkoxy equivalents of these, especially methoxy and ethoxy. Benzyloxy is a particularly preferred alkoxy group substituted by phenyl.

Preferably, at least one of $R^4$ and $R^5$ and, independently, at least one of $R^1$, $R^2$, $R^3$ and $R^7$ represents an alkyl group.

When one or more of $R^1$, $R^2$, $R^3$, $R^4$, $R^5$ and $R^7$ represents acyl or acylamino, the acyl moiety is desirably an alkanoyl moiety, especially of 2 to 4 carbon atoms. Acetyl and acetylamino are particularly preferred.

Desirably, at least one of $R^1$, $R^2$, $R^3$ and $R^7$ represents acyl.

Desirably at least one of $R^1$, $R^2$, $R^3$ and $R^7$ represents hydroxy.

When one or more of $R^1$, $R^2$, $R^3$, $R^4$, $R^5$ and $R^7$ represents alkenyl it is preferably of 2 to 4 carbon atoms, and is especially vinyl or allyl.

When one or more of $R^1$, $R^2$, $R^3$, $R^4$, $R^5$, and $R^7$ represents halogen, it may preferably be chlorine, bromine or iodine, chlorine and bromine being especially preferred.

At least one, and at most three, of $R^1$, $R^2$, $R^3$ and $R^7$ preferably represent hydrogen.

At least one of $R^4$ and $R^5$ preferably represents hydrogen.

$R^4$ is preferably in the 6- or 8-position when it represents other than hydrogen.

The group X is preferably of 3 to 7 carbon atoms, and may be straight or branched. It is preferably a straight chain alkylene group optionally substituted by a hydroxy group. Specific preferred groups which X may represent are 1,2-dimethylene, 1,3-trimethylene and 2-hydroxy-1,3-trimethylene.

A preferably represents oxygen.

The group Q is preferably alkylene or alkenylene of 2 to 4 carbon atoms and is desirably a straight chain group, e.g. ethenylene, 1,2-dimethylene or 1,3-trimethylene.

The group D is preferably a carboxyl group.

A preferred group of compounds of formula I comprises those wherein the —O.X.A— chain is bonded to the chromone nucleus in the 6- or 7-position (particularly in the 7-position).

A particularly preferred group of compounds comprises those wherein $R^1$ represents hydrogen or alkanoyl of 2 to 4 carbon atoms, $R^2$ represents hydrogen or hydroxy, $R^3$, $R^4$ and $R^5$ each represent hydrogen or alkyl of 1 to 4 carbon atoms, $R^7$ represents hydrogen, X represents straight chain alkylene of 3 to 7 carbon atoms optionally substituted by a hydroxy group, A represents oxygen, Q represents a straight chain alkylene or alkenylene group of 2 to 6 carbon atoms, and D represents carboxyl, and the salts, esters and amides thereof.

Salts of the compounds of formula I include the alkali-metal and alkaline-earth metal salts, e.g. the potassium, lithium and calcium salts and, notably the sodium salt. Also included are salts with organic bases, e.g. optionally hydroxy-substituted alkylamines, e.g. methylamine and ethylamine, and bases containing both nitrogen and oxygen atoms; specifically salts with alkanolamines, e.g. tri- and di-ethanolamine; hydroxyalkylalkylamines, e.g. tri-(hydroxymethyl)methylamine; 5 or 6 membered nitrogen containing heterocyclic rings, e.g. morpholine; N-alkylamino substituted sugars, e.g. N-methylglucamine; and amino acids, e.g. lysine, ornithine or arginine.

Esters within the scope of the invention include alkyl esters, especially of 1 to 6 carbon atoms, e.g. the methyl and ethyl esters.

Specific preferred compounds of the invention are those of the Examples provided hereinafter.

According to our invention we also provide a process for the production of a compound of formula I, or a pharmaceutically acceptable salt, ester or amide thereof, from a compound of formula:

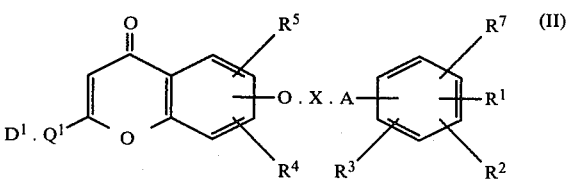

wherein $R^1$, $R^2$, $R^3$, $R^4$, $R^5$, $R^7$, X and A are as defined hereinbefore and $D^1$ and $Q^1$ are as defined hereinafter, which comprises:

(a) hydrolysing a compound where $Q^1$ represents a group Q as defined hereinbefore and $D^1$ represents a group hydrolysable to a carboxyl group to give a compound of formula I where D represents carboxyl or a salt thereof, or (b) reacting a compound where $Q^1$ is absent or represents a group Q as defined hereinbefore of 2 to 4 carbon atoms and $D^1$ represents —CHO:
 (i) with a compound of formula HOOC—CH=P(R)$_3$ or of formula HOOC—CH$_2$—P(=O) (OR)$_2$ where R represents phenyl or alkyl of 1 to 6 carbon atoms, or an ester or salt of either, or (ii) with malonic acid or an ester thereof and hydrolysing and decarboxylating the product, to give a compound of formula I where Q represents —Q$^1$—CH=CH— and D represents —COOH, or (c) selectively reducing a compound where Q$^1$ represents a group reducible to a group Q, or (d) subjecting to elevated temperature a compound where Q$^1$ is absent or represents a group Q as defined hereinbefore of 2 to 4 carbon atoms and D$^1$ represents —CO.C(COOH)=P(R)$_3$, where R is as defined hereinbefore, or an ester thereof, to give a compound of formula I where Q represents —Q$^1$—C≡C— and D represents —COOH or an ester thereof, or (e) subjecting to the action of a base a compound where Q$^1$ is absent and D$^1$ represents —C(OSO$_2$A$^1$)=C(COOR)$_2$ where R is as defined hereinbefore and A$^1$ represents an aromatic moiety, to give a salt of a compound of formula I where Q represents —C≡C— and D represents —COOH, or (f) salifying, esterifying or amidating a compound where D$^1$ represents a free acidic group to give a salt, ester or amide of a compound of formula I, or converting a compound where D$^1$ represents cyano to the corresponding tetrazole, or converting a compound where D$^1$ represents a free carboxyl group or an acid halide, ester or mixed anhydride thereof to the corresponding carboxamidotetrazole.

We also provide a process for the preparation of compounds of formula I which comprises reacting a compound of the formula:

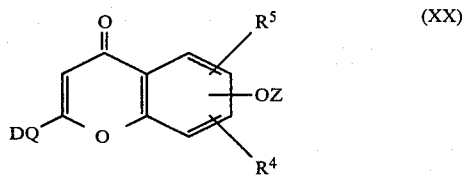

with a compound of the formula:

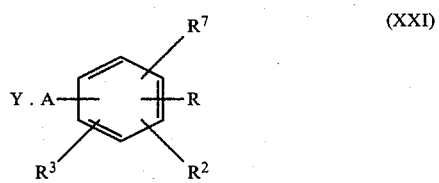

wherein R$^1$, R$^2$, R$^3$, R$^4$, R$^5$, R$^7$, D, Q and A are as defined hereinbefore, and Y and Z represent the pair of groups (i) hydrogen or a reactive metal and (ii) a hydrocarbon chain of 1 to 10 carbon atoms carrying an anion forming group or an epoxide group.

We also provide a process for the preparation of compounds of formula I which comprises cyclising a compound of the formula:

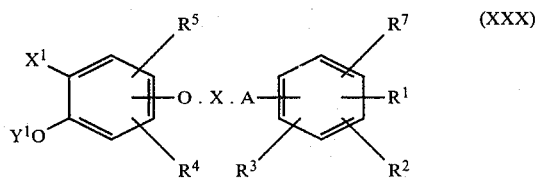

wherein R$^1$, R$^2$, R$^3$, R$^4$, R$^5$, R$^7$, X and A are as defined hereinbefore, X$^1$ represents a group —COCH$_2$COQD$^1$ where Q is as defined hereinbefore, D$^1$ represents a group D as defined hereinbefore (or a salt, ester or amide thereof), and Y$^1$ represents hydrogen or a displaceable protecting group (e.g. alkyl, silyl or aralkyl).

The cyclisation may conveniently be effected by means of an acid, e.g. a mineral acid, for example a hydrohalic acid such as hydrochloric acid or hydrobromic acid.

Where D$^1$ represents a salt, ester or amide, this may be converted by the action of th acid to the free acidic group D.

In process (a) the group D$^1$ may be, for example, an alkoxy (C 1 to 10) carbonyl group, a carboxamide group, a mono- or di- alkyl- (C 1 to 10) carboxamido group, or an N-phenylcarboxamido group. The hydrolysis may be carried out using conventional techniques, for example under acidic or under alkaline conditions. The reaction may conveniently be carried out in a suitable aqueous solvent, for example an aqueous lower alkanol, at a temperature of from about 20° to 120° C.

In process (b) (i) the reaction may be carried out in the presence of a non nucleophilic base, e.g. sodium hydride or methyl lithium. The reaction may be carried out in a solvent which is inert under the reaction conditions, for example benzene, dimethylformamide or dimethoxyethane. The reaction may be carried out at a temperature of from about 15° to 150° C.

In process (b) (ii) the reaction may be carried out in the presence of a basic catalyst and in a solvent (which when the solvent is basic may also act as catalyst) for example pyridine, or titanium tetrachloride. The reaction is preferably carried out at a temperature of from about 60° to 120° C.

In process (c), the group Q$^1$ preferably represents alkenylene or alkynylene giving, respectively compounds of formula I where Q represents alkylene and alkenylene (which may be further reduced to alkylene if desired). The reduction may be carried out using conventional techniques for the selective reduction of such compounds, e.g. catalytic hydrogenation in a suitable solvent, e.g. ethanol or acetic acid, at atmospheric pressure and using a palladium on charcoal or a palladium on barium sulphate catalyst (Lindlar's catalyst).

The reaction of process (d) may be carried out at a temperature of from about 200° to 300° C. The reaction is preferably carried out by simply heating the compound of formula II.

The reaction of process (e) is conveniently effected by means of an alkali-metal hydroxide, e.g. sodium or potassium hydroxide in a suitable solvent medium, e.g. water.

The cyclisation of the compounds of formula XXX is conveniently effected by heating a solution of the compound of formula XX in an appropriate solvent medium, e.g. an alkanol such as methanol, and by adding the appropriate acid. Desirably the acid is a hydro- halic acid, especially hydrochloric acid, and the reaction is effected by passing the gaseous hydrogen halide through the solution.

The salts of the present invention may be prepared by treating a compound of formula I, an ester or an amide thereof, or another salt thereof with an appropriate base, e.g. an alkali-metal base, or with an appropriate salt by a metathetical process. The tetrazoles and carboxamidotetrazoles may be prepared from the corresponding carboxylic acids by processes known per se, e.g. via the corresponding acid halides, amides and cyanides.

In the reaction between compounds of formulae XX and XXI, when Y or Z is a reactive metal the metal may be, for example, an alkali-metal, e.g. sodium or another reactive metal, e.g. thallium. When Y or Z represents a hydrocarbon chain carrying an anion forming group the anion forming group may be, for example, a halogen atom, e.g. bromine, or a sulphonate group, e.g. a methyl sulphonate or a p-toluenesulphonate group. When Y or Z represents a hydrocarbon chain carrying a halogen atom the reaction may be carried out in the presence of a solvent which is inert under the reaction conditions, e.g. acetone and in the presence of an acid acceptor, e.g. potassium carbonate. The reaction is also preferably carried out under anhydrous conditions and in the presence of a suitable catalyst, e.g. KI. When Y or Z represent a hydrocarbon group carrying an epoxide, the reaction may be carried out at an elevated temperature in a solvent which is inert under the reaction conditions, e.g. dioxan or dimethylformamide, and in the presence of a suitable catalyst, e.g. trimethylbenzylammonium hydroxide. Alternatively, the reaction may be carried out at an elevated temperature in a tertiary alcohol, e.g. t-butanol or 1,1-dimethylpropan-1-ol and in the presence of the potassium salt of the alcohol, or in the presence of an alkali-metal hydroxide in a suitable solvent, e.g. an alkanol such as ethanol.

The compounds of formula I may be recovered from their reaction mixtures by using conventional techniques.

The starting materials of formula II for processes (a), (c) and (f) may be made by appropriate processes analogous to processes (a), (b), (c), (d) or (e), or by converting, e.g. esterifying a corresponding compound of formula I.

The starting materials of formula II for process (b) are either known compounds or may be made from known compounds using conventional techniques known per se.

The starting materials of formula II for process (d) may be made by reacting a compound of the formula:

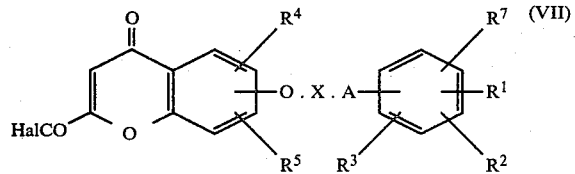

in which
$R^1$, $R^2$, $R^3$, $R^5$, $R^4$, $R^7$ and X are as defined above, and Hal represents halogen
with a compound of the formula HOOC—CH=P(R)$_3$ or an ester thereof.

The starting materials of formula II for process (e) may be prepared by reacting a compound of formula VII with the anion of a dialkyl malonate, and heating the resulting product with an arene sulphonic anhydride.

The compounds of formula XX may be made from known compounds using processes analogous to processes described above.

The compounds of formula XXX may be made by reacting a compound corresponding to formula XXX wherein $X^1$ is acetyl with a compound $D^1QCOZ$ where Z is an anionic leaving group (e.g. halogen or alkoxy) in the presence of a suitable base and inert solvent. The base may be for example sodium hydride, and suitable solvents include dioxan and dimethylformamide.

Some of the groups $R^1$ to $R^7$ and X may be affected by the reaction conditions described above. Where necessary or desirable, therefore, the reaction may be carried out using protected derivatives of the reagents.

The processes described above may produce the compound of formula I or a derivative thereof. It is also within the scope of this invention to treat any derivative so produced to liberate the free compound of formula I, or to convert one derivative into another.

Those compounds of formula I in which Q represents an alkenylene group may exist as cis or trans isomers.

The compounds of formula I and their pharmaceutically-acceptable derivatives are useful because they possess pharmacological properties. In particular, the compounds are antagonists of the slow-reacting substance of anaphylaxis (SRS-A), or its pathological effects, as is indicated by their activity in the test set out in Example A. The compounds also antagonise the effects of SRS-A obtained during antigen challenge of sensitised human chopped lung on isolated guinea pig ileum as described in Example A. The compounds also have the same utility at the same dosages as the compounds of Dutch Patent Specification No. 68,11740.

The compounds are thus useful in the treatment of disorders in which SRS-A is a factor, for example skin afflictions, hay fever, chronic bronchitis, obstructive airways diseases, e.g. asthma, allergic conditions of the eye and allergic conditions of the gastro-intestinal tract, e.g. food allergies.

For the above-mentioned uses, the dosage administered will, of course, vary depending upon the compound employed, mode of administration and treatment desired. However, in general, satisfactory results are obtained when administered at a daily dosage of from about 1 milligram to about 10 milligrams per kilogram of animal body weight, preferably given in divided doses 2 to 4 times a day or in sustained release form. For the larger mammals, the total daily dosage is in the range of from about 50 milligrams to about 700 milligrams, and dosage forms suitable for administration comprise from about 12 milligrams to about 350 milligrams of the compound admixed with a solid or liquid pharmaceutical carrier or diluent. The compounds may be administered during or before the attack of the disorder to be treated.

The compounds may be administered in admixture with a pharmaceutically acceptable adjuvant, diluent or carrier, the composition used depending on many factors including the disorder to be treated. The compounds may be administered parenterally, by inhalation, topically or orally.

The invention is illustrated, but in no way limited by the following Examples, in which temperatures are in °C.

EXAMPLE 1 trans-Sodium 3-[7-[3-(4-acetyl-3-hydroxy-2-n-propyl phenoxy)-2-hydroxypropyloxy]-4-oxo-8-n-propyl-4H-1-benzopyran-1-yl]acrylate (a) 4-Benzyloxy-2-hydroxy-3-propylacetophenone 2,4-Dihydroxy-3-propylacetophenone (48.5 g), benzyl bromide (30 ml), anhydrous potassium carbonate (38 g) and potassium iodide (0.2 g) in butan-2-one (300 ml) were refluxed for 16 hours. The hot mixture was filtered, and the filtrate was evaporated. The residue was dissolved in ethyl acetate and washed with 5% sodium hydroxide solution, and water, dried and evaporated to a solid, which crystallised from cyclohexane to afford the title compound (27.3 g), mp 78°.

(b) 7-Benzyloxy-3-diethoxymethyl-8-propyl-4H-1-benzopyran-4-one

To a stirred mixture of 4-benzyloxy-2-hydroxy-3-propylacetophenone (14.2 g) and sodium hydride (5.3 g of a 50% dispersion in oil) in dry toluene (200 ml) heated under reflux under nitrogen was added dropwise a solution of ethyl diethoxyacetate (7.9 g) in toluene (100 ml). The mixture was refluxed for 4 hours and then the ethanol which had formed was removed by azeotropic distillation. The mixture was evaporated to a sticky solid, which was washed with light petroleum (bp 40°–60°), and then dissolved in ether. The ether was washed with dilute hydrochloric acid and brine, dried and evaporated to give the intermediate diethyl-diketo acetal. This solid (5.0 g) was refluxed in ethanolic hydrogen chloride (200 ml) for 45 minutes. The solution was evaporated, and the residue was triturated with ether and chromatographed on silica gel with chloroform to yield the benzopyran acetal (10.6 g), mp 95°–97°.

(c) 7-Benzyloxy-4-oxo-8-propyl-4H-1-benzopyran-2-carboxaldehyde

7-Benzyloxy-2-diethoxymethyl-8-propyl-4H-1-benzopyran-4-one (5.0 g) was dissolved in glacial acetic acid (50 ml), and 10% sulphuric acid (25 ml) was added. Steam was passed through the solution for 30 minutes. On cooling the yellow crystals which formed were filtered off, washed with light petroleum (bp 40°–60°), chromatographed on silica gel with ether, and then crystallised from ether to give the aldehyde (1.67 g), mp 150°.

(d) trans-Ethyl 3-(7-benzyloxy-4-oxo-8-n-propyl-4H-1-benzopyran-2-yl)acrylate

A solution of 7-benzyloxy-4-oxo-8-n-propyl-4H-1-benzopyran-2-carboxaldehyde (1.0 g) in dry benzene (30 ml) was added to a stirred solution of carbethoxymethylene-triphenylphosphorane (1.1 g) in dry benzene (50 ml). After 1 hour the solvent was evaporated and the remaining white solid was extracted several times with ether. The combined and concentrated ether washings were chromatographed over silica gel (100 g). Elution with ether afforded a white solid which was crystallised from ether to yield trans ethyl 3-(7-benzyloxy-4-oxo-8-n-propyl-4H-1-benzopyran-2-yl)acrylate (0.45 g) mp 140° C., a compound of the invention.

(e) trans Ethyl 3-(7-hydroxy-4-oxo-8-n-propyl-4H-1-benzopyran-2-yl)acrylate

A solution of ethyl 3-(7-benzyloxy-4-oxo-8-n-propyl-4H-1-benzopyran-2-yl)acrylate (6.0 g) in dichloromethane (150 ml) at −60° C. was treated with an excess of $BCl_3$. After ¾ hour the solution was poured onto ice and stirred. After 12 hours the mixture was extracted with ethyl acetate. The organic layer was separated, washed well (water), dried ($MgSO_4$) and evaporated to afford a pale yellow solid. The latter was crystallised from aqueous ethanol to yield trans ethyl 3-(7-hydroxy-4-oxo-8-n-propyl-4H-1-benzopyran-2-yl)acrylate (3.2 g) mp 203°–204° C.

(f) trans-Ethyl 3-[7-[3-(4-acetyl-3-hydroxy-2-n-propylphenoxy)-2-hydroxypropyloxy]-4-oxo-8-n-propyl-4H-1-benzopyran-2-yl]acrylate 4-(2,3-Epoxy)-n-propyloxy-2-hydroxy-3-n-propylacetophenone (2.75 g) was added to a stirred refluxing solution of trans-ethyl 3-(7-hydroxy-4-oxo-8-n-propyl-4H-1-benzopyran-2-yl)acrylate (3.2 g) and tert-amylalkoxide (0.76 g) in tert-amylalcohol (500 ml). After 5 days the solution was poured into water, acidified and extracted with ethyl acetate. The organic layer was extracted ($NaHCO_3$ solution), washed (saturated NaCl solution), dried ($MgSO_4$) and evaporated to afford a brown solid. The latter was chromatographed over silica gel (500 g). Elution with ether afforded a white solid which was crystallised from acetone-ether to yield trans-ethyl 3-[7-[3-(4-acetyl-3-hydroxy-2-n-propylphenoxy)-2-hydroxy propyloxy]-4-oxo-8-n-propyl-4H-1-benzopyran-2-yl]acrylate (1.56 g) mp 125°–127° C.

(g) trans-3[7-[3-(4-Acetyl-3-hydroxy-2-n-propylphenoxy)-2-hydroxypropyloxy]-4-oxo-8-n-propyl-4H-1-benzopyran-2-yl]acrylic acid A solution of trans-ethyl 3-[7-[3-(4-acetyl-3-hydroxy-2-n-propylphenoxy)-2-hydroxypropyloxy]-4-oxo-8-n-propyl-4H-1-benzopyran-2-yl]acrylate (1.56 g) and sodium hydrogen carbonate (1.56 g) in aqueous ethanol was refluxed for 1 hour. Ethanol was removed by distillation and the residual aqueous solution cooled. Acidification afforded a gum which solidified on prolonged treatment with refluxing carbon tetrachloride. Crystallisation from acetone-carbon tetrachloride yielded trans-3[7-[3-(4-acetyl-3-hydroxy-2-n-propylphenoxy)-2-hydroxypropyloxy]-4-oxo-8-n-propyl-4H-1-benzopyran-2-yl]acrylic acid (0.58 g) mp 101°–103° C.

(h) trans-Sodium 3-[7-[3-(4-acetyl-3-hydroxy-2-n-propylphenoxy)-2-hydroxypropyloxy]-4-oxo-8-n-propyl-4H-1-benzopyran-2-yl]acrylate Sodium hydrogen carbonate (0.084 g) was added to a suspension of trans-3-[7-[3-(4-acetyl-3-hydroxy-2-n-propylphenoxy)-2-hydroxypropyloxy]-4-oxo-8-n-propyl-4H-1-benzopyran-2-yl]acrylic acid (0.58 g) in water (30 ml) and solution effected by heating. The cooled solution was freeze dried to yield trans-sodium-3-[7-[3-(4-acetyl-3-hydroxy-2-n-propylphenoxy)-2-hydroxypropyloxy]-4-oxo-8-n-propyl-4H-1-benzopyran-2-yl]acrylate (0.59 g).

$C_{29}H_{31}NaO_9$ 1.5 $H_2O$ requires: C 60.3; H 6.0%; found: C 60.3; H 6.1%

EXAMPLE 2

Sodium 3-[7-[3-(4-acetyl-3-hydroxy-2-n-propylphenoxy)-2-hydroxypropyloxy]-4-oxo-8-n-propyl-4H-1-benzopyran-2-yl]propionate (a) Ethyl 3-[7-[3-(4-acetyl-3-hydroxy-2-n-propyl phenoxy)-2-hydroxypropyloxy]-4-oxo-8-n-propyl-4H-1-benzopyran-2-yl]propionate trans-Ethyl 3-[7-[3-(4-acetyl-3-hydroxy-2-n-propyl phenoxy)-2-hydroxypropyloxy]-4-oxo-8-n-propyl-4H-1-benzopyran-2-yl]acrylate (1.2 g) in dioxan was hydrogenated, over a palladium-charcoal catalyst, at atmospheric pressure and ambient temperature. The catalyst was removed by filtration and the concentrated filtrate chromatographed over silica-gel (60 g). Elution with ether afforded a white solid which was crystallised from etherpetrol (40°–60°) to yield ethyl 3-[7-[3-(4-acetyl-3-hydroxy-2-n-propylphenoxy)-2-hydroxypropyloxy]-4-oxo-8-n-propyl-4H-1-benzopyran-2-yl]propionate (0.79 g), mp 137°–138° C.

(b) 3-[7-[3-(4-acetyl-3-hydroxy-2-n-propylphenoxy)-2-hydroxypropyloxy]-4-oxo-8-n-propyl-4H-1-benzopyran-2-yl]propionic acid A solution of ethyl 3-[7-[3-(4-acetyl-3-hydroxy-2-n-propylphenoxy)-2-hydroxypropyloxy]-4-oxo-8-n-propyl-4H-1-benzopyran-2-yl]propionate (0.79 g) and sodium carbonate (0.79 g) in aqueous ethanol was refluxed for 1 hour. Ethanol was removed by distillation and the residual aqueous solution cooled. Acidification afforded a gum which solidified on prolonged treatment with refluxing ether. Crystallisation from acetone-ether yielded 3-[7-[3-(4-acetyl-3-hydroxy-2-n-propylphenoxy)-2-hydroxypropyloxy]-4-oxo-8-n-propyl-4H-1-benzo pyran-2-yl]propionic acid (0.53 g) mp 79°–80° C. The sodium salt was prepared therefrom by the method of Example 1(h).

Sodium salt analysis: $C_{29}H_{33}NaO_9$ $2H_2O$ requires: C 59.2; H 6.3%; found: C 59.2; H 6.5%

EXAMPLE 3

Sodium 3-[7-Benzyloxy-4-oxo-8-propyl-4H-1-benzopyran-2-yl]propionate (a) Methyl 3-[7-benzyloxy-4-oxo-8-propyl-4H-1-benzopyran-2-yl]propionate Sodium hydride (13.2 g of a 50% dispersion in oil) was washed with ether and suspended in dry dimethyl formamide (300 ml). To the suspension at 0° was added 4-benzyloxy-2-hydroxy-3-propylacetophenone (61 g) slowly with stirring. When the mixture became clear, 3-methoxy carbonyl propionyl chloride (39 g) in dimethylformamide (100 ml) was added slowly, and the mixture was stirred at room temperature for 48 hours. The mixture was carefully poured onto a slurry of ice and dilute hydrochloric acid. Extraction was effected with ethyl acetate, followed by washing with saturated sodium bicarbonate solution, and water. Drying and evaporation gave 6-acetyl-3-benzyloxy-2-propylphenyl methyl succinate as a dark oil (93 g).

The oil was slowly added with stirring to a suspension of sodium hydride (24 g of a 50% dispersion in oil) in dry dioxan (200 ml) at 70°. After 30 minutes the mixture was cooled and carefully added to a mixture of ice and dilute hydrochloric acid.

The mixture was extracted with ethyl acetate, washed well with water and evaporated to yield methyl 6-(4-benzyloxy-2-hydroxy-3-propylphenyl)-4,6-dioxohexanoate (65 g) as a dark solid. Pmr and mass spectra were in accordance with the structure.

The solid was dissolved in methanol boiling under reflux and gaseous hydrogen chloride was bubbled through the solution for 30 minutes.

After a further 30 minutes at reflux the mixture was poured onto ice and extracted with ethyl acetate, which was then washed with water and sodium bicarbonate solution, dried and evaporated to a solid (32 g). The solid was chromatographed on silica gel with chloroform, and the relevant fractions were crystallised from cyclohexane to afford the title ester as needles, mp 88°–89°.

(b) 3-[7-Benzyl-4-oxo-8-propyl-4H-1-benzopyran-2-yl]propionic acid

Methyl 3-[7-benzyl-4-oxo-8-propyl-4H-1-benzopyran-2-yl]propionate (1.0 g) was refluxed with ethanol (50 ml) containing 10% aqueous sodium carbonate solution (10 ml) for 30 minutes. The mixture was diluted with water, washed with ethyl acetate, and acidified to give a solid, which crystallised from ethanol to give the propionic acid (0.7 g), mp 160°–161°.

(c) Sodium 3-[7-benzyl-4-oxo-8-propyl-4H-1-benzopyran-2-yl]propionate

3-[7-Benzyl-4-oxo-8-propyl-4H-1-benzopyran-2-yl]propionic acid was dissolved in ethanol and treated with an equivalent of aqueous sodium bicarbonate and the clear resulting solution was evaporated. The residue was dissolved in water and freeze-dried to afford the sodium salt.

$C_{22}H_{21}NaO_5 \cdot H_2O$ requires: C, 65.0; H, 5.7; found: C, 65.0; H, 5.5%

EXAMPLE 4

Sodium 3-[7-(3-(4-acetyl-2-n-butyl-3-hydroxyphenoxy)-2-hydroxypropoxy-4-oxo-8-n-propyl-4H-1-benzopyran-2-yl]propionate (a) Ethyl 3-[7-hydroxy-4-oxo-8-n-propyl-4H-1-benzopyran-2-yl]propionate By a process analogous to that of Example 3(a) was prepared ethyl 3-[7-benzyloxy-4-oxo-8-propyl-4H-1-benzopyran-2-yl]propionate. This compound (1.0 g) in dry dichloromethane (30 ml) at −78° C. was treated with boron trichloride (2 ml). After 20 minutes, the mixture was poured onto ice and extracted with 10% aqueous sodium carbonate. Acidification gave a solid which crystallised from ethyl acetate to give the desired product (0.35 g), mp 127°–128° C.

(b) 3-n-Butyl-2,4-dimethoxyacetophenone 2-n-Butyl-1,3-dimethoxybenzene (27 g) and acetyl chloride (20 ml) in 1,2-dichloroethane (200 ml) at −20° were stirred and treated with titanium tetrachloride (70 ml) slowly over 30 minutes. The red solution was allowed to warm to room temperature over 2 hours, and poured onto ice. The organic phase was washed with water and evaporated to an oil, which was distilled at 130°–132°/0.08 mm.Hg, to afford the acetophenone (26.1 g).

(c) 3-n-Butyl-2,4-dihydroxyacetophenone 3-n-Butyl-2,4-dimethoxyacetophenone (32 g) in dry methylene chloride (200 ml) was cooled to −78° and treated dropwise with boron tribromide (40 ml) over 30 minutes. The mixture was allowed to warm to room temperature, stirred for 30 hours, poured onto ice, and extracted with chloroform, which was then dried and evaporated to a solid (20 g). Distillation at 250° at 0.07 mm gave the dihydroxyacetophenone, mp 85°–85.5°.

(d) (4-Acetyl-2-n-butyl-3-hydroxyphenoxy)methyloxiran 3-n-Butyl-2,4-dihydroxyacetophenone (10 g) and epichlorohydrin (12 ml) in ethanol (100 ml) were refluxed under nitrogen. Potassium hydroxide (2.8 g) was added and the mixture was refluxed for 5.5 hours. The mixture was poured into water, acidified, and extracted with ether, which was washed with 2% sodium hydroxide solution, and water, dried and evaporated to give an oil. The oil was distilled at 230°/0.07 mm to give (4-acetyl-2-n-butyl-3-hydroxyphenoxy)methyloxiran as an oil (11 g). The pmr spectrum was consistent with the structure.

(e) Ethyl 3-[7-(3-(4-acetyl-2-n-butyl-3-hydroxyphenoxy)-2-hydroxypropyloxy)-4-oxo-8-propyl-4H-1-benzopyran-2-yl]propionate To sodium hydroxide (0.6 g) in ethanol (200 ml) was added (4-acetyl-2-n-butyl-3-hydroxyphenoxy)methyloxiran (6 g) and ethyl 3-(7-hydroxy-4-oxo-8-propyl-4H-1-benzopyran-2-yl)propionate (4.56 g). The mixture was refluxed for 6 hours, evaporated to ⅓ volume and acidified. Extraction with ethyl acetate and subsequent washing with 10% sodium hydroxide solution, and water, and evaporation gave a red oil which was chromatographed on silica with chloroform:ethyl acetate (12:1) mixture to yield a solid. Recrystallisation from ethyl acetate/cyclohexane mixture afforded the title ester as buff micro needles (2.3 g), mp 118°–118.5°.

(f) 3-[7-(3-(4-Acetyl-2-n-butyl-3-hydroxyphenoxy)-2-hydroxypropoxy)-4-oxo-8-propyl-4H-1-benzopyran-2-yl]propionic acid By a method analogous to that of Example 2(b), the above acid was liberated from the ethyl ester as a solid, mp 175°–176° C. The sodium salt thereof was prepared by a method analogous to that of Example 1(h).

EXAMPLES 5–16

By methods analogous to those described in Examples 1–4 the following compounds were prepared:

5. 3-[7-(3-(4-Acetyl-3-hydroxy-2-n-propylphenoxy)-2-hydroxypropoxy-4-oxo-6-n-propyl-4H-1-benzopyran-2-yl]propionic acid, and the ethyl ester and sodium salt thereof.
Mp (free acid)=145°–146° C., mp (ethyl ester)=105°–106° C.

6. 4-[7-(3-(4-Acetyl-3-hydroxy-2-n-propylphenoxy)-2-hydroxypropoxy-4-oxo-8-n-propyl-4H-1-benzopyran-2-yl]butyrate and the methyl ester and sodium salt thereof.
Mp (free acid)=107°=108° C., mp (methyl ester)=121°–122° C.

7.* 3-[7-(3-(4-Acetyl-3-hydroxy-2-n-propylphenoxy)-propoxy)-4-oxo-8-n-propyl-4H-1-benzopyran-2-yl]propionic acid and the ethyl ester and lysine salt thereof.
Mp (ethyl ester)=99°–100° C.
*In the preparation of this compound 4-(3-bromophenoxy)-2-hydroxy-3-propylacetophenone was employed instead of an oxiran in the reaction to link the ring nuclei.

8. 3-[7-(2-(4-Acetyl-3-hydroxy-2-n-propylphenoxy)ethoxy)-4-oxo-8-n-propyl-4H-1-benzopyran-2-yl]propionic acid and the ethyl ester and sodium salt thereof.
Mp (free acid)=153°–154° C.

9. 3-[7-(3-(2-n-propylphenoxy)-2-hydroxypropoxy)-4-oxo-8-n-propyl=4H-1-benzopyran-2-yl]propionic acid and the sodium salt thereof.
Mp (free acid)=112°–114° C.

10. 3-[7-(3-(2-Acetyl-3-hydroxyphenoxy)propoxy)-4-oxo-8-n-propyl-4H-1-benzopyran-2-yl]propionic acid and the sodium salt thereof.
Mp (free acid)=173°–174° C.

11. 3-[7-(3-(4-Acetyl-3-hydroxy-2-n-propylphenoxy)-2-hydroxypropoxy)-8-methyl-4-oxo-4H-1-benzopyran-2-yl]propionate and the ethyl ester and sodium salt thereof.
Mp (ethyl ester)=155–156° C., mp (free acid)=142°–145° C.

12. 3-(6-Benzyloxy-4-oxo-4H-1-benzopyran-2-yl)propionic acid, mp (free acid)=161°–163° C.

13. 3-[7-(2-Hydroxy-3-(4-methylphenyloxy)propyloxy)-4-oxo-8-propyl-4H-1-benzopyran-2-yl]propionic acid, mp (free acid)=111°–113° C. (decomp.).

14. 3-[7-(6-(4-Bromophenyloxy)hexyloxy)-4-oxo-8-propyl-4H-1-benzopyran-2-yl]propionic acid, mp (free acid)=125°–127° C., mp (ethyl ester)=87°–88° C.

15. 6-[7-(3-(4-Acetyl-3-hydroxy-2-propylphenoxy)-2-hydroxy-propoxy)-4-oxo-8-propyl-4H-1-benzopyran-2-yl]hexanoic acid, mp (free acid)=95°–96° C.

16. 3-[4-Oxo-7-(5-phenylpentyloxy)-8-propyl-4H-1-benzopyran-2-yl]propionic acid, mp (free acid)=125°–126° C.

EXAMPLE 17

3-(7-Benzyloxy-4-oxo-8-n-propyl-4H-1-benzopyran-2-yl)acrylic acid

7-Benzyloxy-4-oxo-8-propyl-4H-1-benzopyran-2-carboxaldehyde (3.2 g), from Example 1(c) and malonic acid (1.1 g) were heated in pyridine (15 ml) at 100° C. until gas evolution ceased. The mixture was then evaporated and the residue was extracted with sodium bicarbonate. Acidification gave the title acid. The same acid was also prepared by hydrolysis of the product of Example 1(d).

EXAMPLE 18

3-[7-(3-Phenoxypropyloxy)-4-oxo-4H-1-benzopyran-2-yl]propiolic acid (a) 7-(3-Phenoxypropyloxy)-4-oxo-4H-1-benzopyran-2-carbonyl chloride and two equivalents of carbomethoxymethylene triphenylphosphorane were stirred overnight in benzene. The precipitate was collected and heated under vacuum at 280° for 1 hour to give the propiolic methyl ester, which was hydrolysed to give the title acid.

(a') The carbonyl chloride used in part (a) was added to one equivalent of diethyl ethoxymagnesiomalonate in dry 1,2-dichloroethane. The mixture was refluxed for 30 minutes, then treated with dilute acid. Isolation and evaporation of the organic phase gave the acylmalonate which was added to one equivalent of potassium t-butoxide and benzenesulphonic anhydride in t-butanol. The mixture was then refluxed for 2 hours and evaporated. Partitioning the residue between ethyl acetate and dilute sodium hydroxide gave, in the organic phase, the enol sulphonate which was stirred overnight in dioxan containing an excess of aqueous sodium hydroxide to afford, on acidification, the title product.

EXAMPLE 19

(a)

3-[7-(3-Phenoxypropyloxy)-4-oxo-4H-1-benzopyran-2-yl]acrylic acid

3-[7-(3-Phenoxypropyloxy)-4-oxo-4H-1-benzopyran-2-yl]propiolic acid (1 g) in ethanol was hydrogenated at atmospheric pressure in the presence of palladium on barium sulphate poisoned with quinoline. Isolation procedures yielded the title acrylic acid.

(b)

3-[7-(3-Phenoxypropyloxy)-4-oxo-4H-1-benzopyran-2-yl]propionic acid

Hydrogenation of the acrylic acid product of stage (a) in ethanol with 5% palladium-charcoal gave, on isolation, the title propionic acid.

EXAMPLE A

The procedure set out below is used to assess the effectiveness of a compound in antagonising SRS-A. The test makes use of the agonist (contractile) effect of SRS-A on isolated guinea-pig ileum.

A satisfactory preparation of SRS-A can be obtained from egg albumen sensitised guinea-pigs. Three weeks after sensitisation, the lungs from such guinea-pigs are removed, perfused free of blood, and chopped. Samples of washed, chopped lung are then challenged with egg albumen (antigen) solution. The supernatants collected 15 minutes after addition of antigen contains histamine and SRS-A and can be used, in the presence of an antihistamine, to induce effects due to SRS-A.

An isolated section of the terminal portion of a guinea-pig ileum is suspended in Tyrode solution, which contains atropine sulphate $10^{-6}$M (700 µg/liter) and mepyramine maleate $10^{-6}$M (400 µg/liter). Atropine sulphate is included to reduce the spontaneous activity of the ileum preparation and to exclude the effects of possible cholinergic agents. Mepyramine maleate is included to exclude the effects of histamine. The composition of the Tyrode solution in g/l distilled water is NaCl 8.0, KCl 0.2, $CaCl_2$ 0.2, $MgCl_2$ 0.1, $NaHCO_3$ 1.0, $NaH_2PO_4 2H_2O$ 0.05 and dextrose 1.0. A 2 ml organ bath is preferred for economy of SRS-A, the tension on the tissue should be about 600 mg and the bathing temperature 37C.

A dose of unpurified SRS-A is selected which produces similar repetitive sub-maximal contractions of the ileum. Each contraction is recorded for 90 seconds when the tissue is washed to allow relaxation. Five minutes is allowed between doses of SRS-A.

The compound under test is added to the organ bath 30 seconds before a dose of SRS-A. A range of concentrations of the compound is chosen to give a log concentration/inhibitory response graph. From this graph, the concentration of compound which would inhibit the ileum contraction to SRS-A by 50% ($IC_{50}$) is determined.

The compounds of Examples 1 to 19 were tested by this procedure. All gave good results.

We claim:

1. The substituted chromones of the formula:

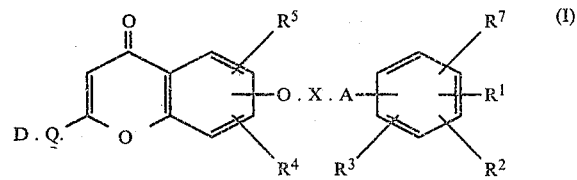

wherein $R^1$, $R^2$, $R^3$, $R^4$, $R^5$ and $R^7$, which may be the same or different, each represent hydrogen, hydroxy, alkyl or alkoxy of 1 to 6 carbon atoms, amino, alkanoyl or alkanoylamino of 2 to 6 carbon atoms, alkenyl of 2 to 6 carbon atoms, halogen, or alkoxy of 1 to 6 carbon atoms substituted by phenyl, X is an alkylene chain of 1 to 10 carbon atoms optionally substituted by a hydroxy group, A is oxygen or is absent, Q represents a straight or branched alkylene, alkenylene, or alkynylene group of 2 to 6 carbon atoms, and D represents carboxy, 5-tetrazolyl or carboxamido-5-tetrazolyl, and pharmaceutically acceptable salts thereof, and pharmaceutically acceptable esters and amides of those compounds where D is carboxy.

2. A compound according to claim 1 wherein at least one of $R^1$, $R^2$, $R^3$ and $R^7$ represents alkyl of 1 to 4 carbon atoms.

3. A compound according to claim 1 wherein at least one of $R^1$, $R^2$, $R^3$ and $R^7$ represents hydroxy or alkanoyl of 2 to 4 carbon atoms.

4. A compound according to claim 1 wherein at least one of $R^4$ and $R^5$ represents alkyl of 1 to 4 carbon atoms.

5. A compound according to claim 1 wherein X represents a straight chain alkylene group of 3 to 7 carbon atoms optionally substituted by a hydroxy group.

6. A compound according to claim 1 wherein Q represents a straight chain alkylene or alkenylene group of 2 to 4 carbon atoms.

7. A compound according to claim 1 selected from the group consisting of:

3-[7-(3-(4-acetyl-3-hydroxy-2-n-propylphenoxy)-2-hydroxypropoxy)-4-oxo-8-n-propyl-4H-1-benzopyran-2-yl]acrylic acid; 3-[7-benzyloxy-4-oxo-8-n-propyl-4H-1-benzopyran-2-yl]propionic acid;

3-[7-(3-(4-acetyl-2-n-butyl-3-hydroxyphenoxy)-2-hydroxypropoxy)-4-oxo-8-n-propyl-4H-1-benzopyran-2-yl]-propionic acid;

3-[7-(3-(4-acetyl-3-hydroxy-2-n-propylphenoxy)-2-hydroxypropoxy)-4-oxo-6-n-propyl-4H-1-benzopyran-2-yl]propionic acid;

4-[7-(3-(4-acetyl-3-hydroxy-2-n-propylphenoxy)-2-hydroxypropoxy)-4-oxo-8-n-propyl-4H-1-benzopyran-2-yl]butyric acid;

3-[7-(3-(4-acetyl-3-hydroxy-2-n-propylphenoxy)-propoxy)-4-oxo-8-n-propyl-4H-1-benzopyran-2-yl]propionic acid;

3-[7-(2-(4-acetyl-3-hydroxy-2-n-propylphenoxy)ethoxy)-4-oxo-8-n-propyl-4H-1-benzopyran-2-yl]propionic acid;

3-[7-(3-(2-propylphenoxy)-2-hydroxypropoxy)-4-oxo-8-n-propyl-4H-1-benzopyran-2-yl]propionic acid;

3-[7-(3-(2-acetyl-3-hydroxyphenoxy)propoxy)-4-oxo-8-n-propyl-4H-1-benzopyran-2-yl]propionic acid;

3-[7-(3-(4-acetyl-3-hydroxy-2-n-propylphenoxy)-2-hydroxypropoxy)-8-methyl-4-oxo-4H-1-benzopyran-2-yl]-propionic acid;

3-(6-benzyloxy-4-oxo-4H-1-benzopyran-2-yl)propionic acid;

3-[7-(2-hydroxy-3-(4-methylphenyloxy)propyloxy)-4-oxo-8-propyl-4H-1-benzopyran-2-yl]propionic acid;

3-[7-(6-(4-bromophenyloxy)hexyloxy)-4-oxo-8-propyl-4H-1-benzopyran-2-yl]propionic acid;

6-[7-(3-(4-acetyl-3-hydroxy-2-propylphenoxy)-2-hydroxypropoxy)-4-oxo-8-propyl-4H-1-benzopyran-2-yl]hexanoic acid;

3-[4-oxo-7-(5-phenylpentyloxy)-8-propyl-4H-1-benzopyran-2-yl]propionic acid;

3-(7-benzyloxy-4-oxo-8-n-propyl-4H-1-benzopyran-2-yl)acrylic acid;

3-[7-(3-phenoxypropyloxy)-4-oxo-4H-1-benzopyran-2-yl]propionic acid;

3-[7-(3-phenoxypropyloxy)-4-oxo-4H-1-benzopyran-2-yl]acrylic acid; and

3-[7-(3-phenoxypropyloxy)-4-oxo-4H-1-benzopyran-2-yl]propionic acid; and pharmaceutically acceptable salts, esters and amides thereof.

8. 3-[7-(3-(4-acetyl-3-hydroxy-2-n-propylphenoxy)-2-hydroxypropoxy)-4-oxo-8-n-propyl-4H-1-benzopyran-2-yl]propionic acid; or a pharmaceutically acceptable salt, ester or amide thereof.

9. A pharmaceutical composition for treating disorders in which the slow-reacting substance of anaphylaxis is a factor which comprises an effective amount of at least one compound according to claim 1 in association with a pharmaceutically-acceptable adjuvant, diluent or carrier.

10. A method of treating a patient suffering from a disorder in which SRS-A is a factor, which comprises administering to that patient an effective amount of at least one compound according to claim 1.

* * * * *

UNITED STATES PATENT AND TRADEMARK OFFICE
CERTIFICATE OF CORRECTION

PATENT NO. : 4,281,008
DATED : July 28, 1981
INVENTOR(S) : TERENCE R. CHAMBERLAIN ET AL.

It is certified that error appears in the above-identified patent and that said Letters Patent are hereby corrected as shown below:

Col. 3, <u>lines</u> 45-50 (formula)

"  should be

--  --

Signed and Sealed this

Third Day of November 1981

[SEAL]

Attest:

GERALD J. MOSSINGHOFF

Attesting Officer    Commissioner of Patents and Trademarks